United States Patent [19]

Beteau et al.

[11] Patent Number: 5,470,745

[45] Date of Patent: Nov. 28, 1995

[54] APPARATUS FOR CONTROLLING THE METHANE FERMENTATION OF ORGANIC MATERIALS

[75] Inventors: Jean-François Beteau, Grenoble; Philippe Graindorge, Gieres, both of France

[73] Assignee: Valorga Process, Vendargues, France

[21] Appl. No.: 284,167

[22] Filed: Aug. 2, 1994

Related U.S. Application Data

[62] Division of Ser. No. 133,029, filed as PCT/FR93/00150, Feb. 12, 1993.

[30] Foreign Application Priority Data

Feb. 12, 1992 [FR] France .................. 92 01577

[51] Int. Cl.⁶ ................................ C12M 1/36
[52] U.S. Cl. ............ 435/286.1; 435/813; 435/303.2; 71/8; 71/10
[58] Field of Search .................. 135/289, 813; 71/8–10

[56] References Cited

U.S. PATENT DOCUMENTS 4,780,415  10/1988  Ducellier et al. .................. 435/166

FOREIGN PATENT DOCUMENTS

| | | |
|---|---|---|
| 0065895 | 12/1982 | European Pat. Off. . |
| 2184035 | 12/1973 | France . |
| 2455629 | 11/1980 | France . |
| 3401889 | 7/1985 | Germany .................. 71/8 |

OTHER PUBLICATIONS

CA 75; 112654, Lawrence, A. W., "Application of Process Kinetics to Design of Anaerobic Process" 1970 (Abstract).
CA 102: 239722, Verrier et al., "Two-Phase Methanization of Solid Vegetable Wastes", 1987 (Abstract).
CA 74: 98180, Babayants et al., "Examination of Parameters . . . ", 1971 (Abstract).
Resources Conservation and Recycling vol. 13, No. 1, 1989, Amsterdam NL pp. 19–32 E. Ten Brummeler et al. The Effect of Several pH Control Chemicals on the Dry Batch Digestion of the Organic Fraction of Municipal Solid Waste.
Chemical Abstracts, vol. 115, No. 1, 8 Jul. 1991, Columbus, Ohio, US; Abst. No. 6910m,. Shioya Suteaki et al. Modeling, Optimization and Realization of Fed–Batch Culture Using the Specific Growth Rate p. 695; Colonne 1; & Kagaku Kogaku Ronbunshu vol. 17, No. 3, 1991, Japan.

Primary Examiner—David A. Redding
Attorney, Agent, or Firm—Steinberg, Raskin & Davidson

[57] ABSTRACT

An apparatus for controlling methane fermentation of organic materials including a main fermentor, sensors associated with the main fermentor for measuring physical-chemical measurements of organic material in the main fermentor, a computer for processing the measurements by using a fermentation model. An additional computer transforms the data of fermentation model into data which affects the operation of the main fermentor. A device is also provided to enable small-scale experimentation in order to adjust the characteristic parameters of the fermentation model incorporated in the computer. The installation allows to maintain the fermentor in optimum biological conditions with a minimum of measurements.

7 Claims, 2 Drawing Sheets

APPARATUS FOR CONTROLLING THE METHANE FERMENTATION OF ORGANIC MATERIALS

This is a division of application Ser. No. 08/133,029, filed Oct. 8, 1993.

BACKGROUND OF THE INVENTION

The present invention relates essentially to a method of controlling the methanic fermentation of various organic materials.

It is also directed to an equipment for carrying out this method.

There has already been proposed to operate fermentors by using mathematical models taking into account the diversity of the materials to be treated as well as the fluctuations of the catalytic behaviors of the micrc-organisms.

It is also known for operating the fermentors to provide an anaerobic fermentation model for diluted substrates or substrates of simple nature but not for concentrated or complex organic materials.

These models may integrate one or several populations of micro-organisms. They may or may not take into account the physical-chemical equilibriums, the inhibiting effect of the pH or of the volatile fatty acids such as the acetic acid which are essential metabolic intermediaries.

There are further known purely biological mathematic models for diluted substrates in one operating step, based upon the acetate concentration or in two operating steps, namely acidogenesis and methanogenesis from simple substrates such as glucose. These models take into account an inhibition of the methanogeneous activity by the non-ionized volatile fatty acids but they do not integrate the pH as a state variable in relation to the physical-chemical balances.

There are further known biological mathematical models for diluted substrates of the methanization taking into account the physical-chemical balances thus permitting to integrate the pH as a state variable and to contemplate its inhibiting part.

These latter models, however, do not take into account the inhibiting effect of the non-ionized volatile fatty acids such as the acetic acid.

But none of the models referred to hereinabove integrates the combination of physical-chemical balances, of the pH as a state variable and of the inhibiting effect of the non-ionized volatile fatty acids and/or takes into account the case of the concentrated or complex organic materials.

It is further known that the operation of industrial methanization fermentors necessarily requires a great number of complementary physical-chemical measurements and analyses and in particular the measurement of:

the amount of the biogas produced and its quality (percentage of methane and percentage of carbon dioxide),
the pH and the temperature,
the quality of the processed inputs and outputs, and
the volatile fatty acids content (AGV) of the fermentation medium and/or the hydrogen percentage of the produced biogas.

In a general manner the operation of the fermentors based upon earlier known models is not satisfactory in that the models are not adjusted to the specific operating conditions of the installation site of the fermentors.

OBJECTS AND SUMMARY OF THE INVENTION

Therefore the object of the present invention is to cope in particular with these inconveniences by providing a method which allows to control the state of the methanic fermentation while being based upon a special model.

For that purpose, the subject of the invention is a method of controlling the methanic fermentation of organic materials in at least one fermentor and of the type consisting in effecting upon the fermentor physical-chemical measurements, processing these measurements in at least one computer permitting with the assistance of a fermentation model to obtain a variable characterizing the biological state of the fermentor and processing this variable to infer or derive therefrom an operation mode of the fermentor, characterized in that the aforesaid physical-chemical measurements are limited to two measurements such for example the pH and the volatile fatty acids content, the aforesaid variable characterizing the biological state is the methanogeneous biological activity and the aforesaid fermentation model is adjusted in accordance with the biomass present in the fermentor and with the organic materials to be treated by the latter.

According to another characterizing feature of this method, the methanogeneous biological activity is expressed by the computer as a specific growth rate ($\mu$) of the methanogeneous bacteria of the biomass of the fermentor.

It should further be specified here that the aforesaid fermentation model is adjusted from an experimentation or testing on a reduced scale which is carried out upon a sample of material taken from the fermentor and which consists in automatically following the evolution of the pH with time and the volatile fatty acids concentration in the fermentor as well as the amounts of methane and carbon dioxide produced.

It is thus already understood that under these conditions a quick and easy adaptation of the model to the operating conditions of the fermentor on its installation site is achieved.

This fermentation model integrates the combination of the biological phenomena including the inhibiting effect of the non-ionized volatile fatty acids and of the physical-chemical balances in the fermentor with the pH as a state variable.

The invention is also directed to an equipment for carrying out the method referred to hereinabove and of the type essentially comprising at least one fermentor, sensors associated with this fermentor to permit physical-chemical measurements to be performed and at least one computer processing these measurements with the assistance of a fermentation model, this equipment being characterized in that with the computer, providing owing to the fermentation model for the conversion of the physical-chemical measurements into a variable characterizing the biological state, is associated another computer providing for the control of at least one of the fermentors and in that the model is adjusted to the biomass present in the fermentor and to the substrate to be treated by an experimenting or testing device on a reduced scale essentially comprising a fermentor containing a sample of material taken from the first-named fermentor, sensors associated with the fermentor and connected to at least one computer providing the values of the parameters allowing to calibrate the aforesaid fermentation model.

The functionalities of the aforesaid computers are gathered within one single and same computer.

This experimenting or testing device may advantageously be located at another place than the installation site of the fermentor.

It should further be specified that the sensors of the testing or experimenting device are adapted to continuously measure the pH, the amounts of $CH_4$ and of $CO_2$ produced and the concentration of volatile fatty acids in the fermentor whereas the parameters provided by the aforesaid computer are:

the maximum methanogenous specific growth rate,
the constant of inhibition of the methanogeneous bacteria,
the saturation constant of the methanogeneous bacteria, and
the yields or efficiency outputs expressed as the $CH_4$/biomass ratio, as the $CO_2$/biomass ratio and as the substrate/biomass ratio.

BRIEF DESCRIPTION OF THE DRAWINGS

The invention will be better understood and further characterizing features, details and advantages thereof will appear better in the following explanatory description with reference to the accompanying diagrammatic drawings given by way of example only and in which.

Figure 3:
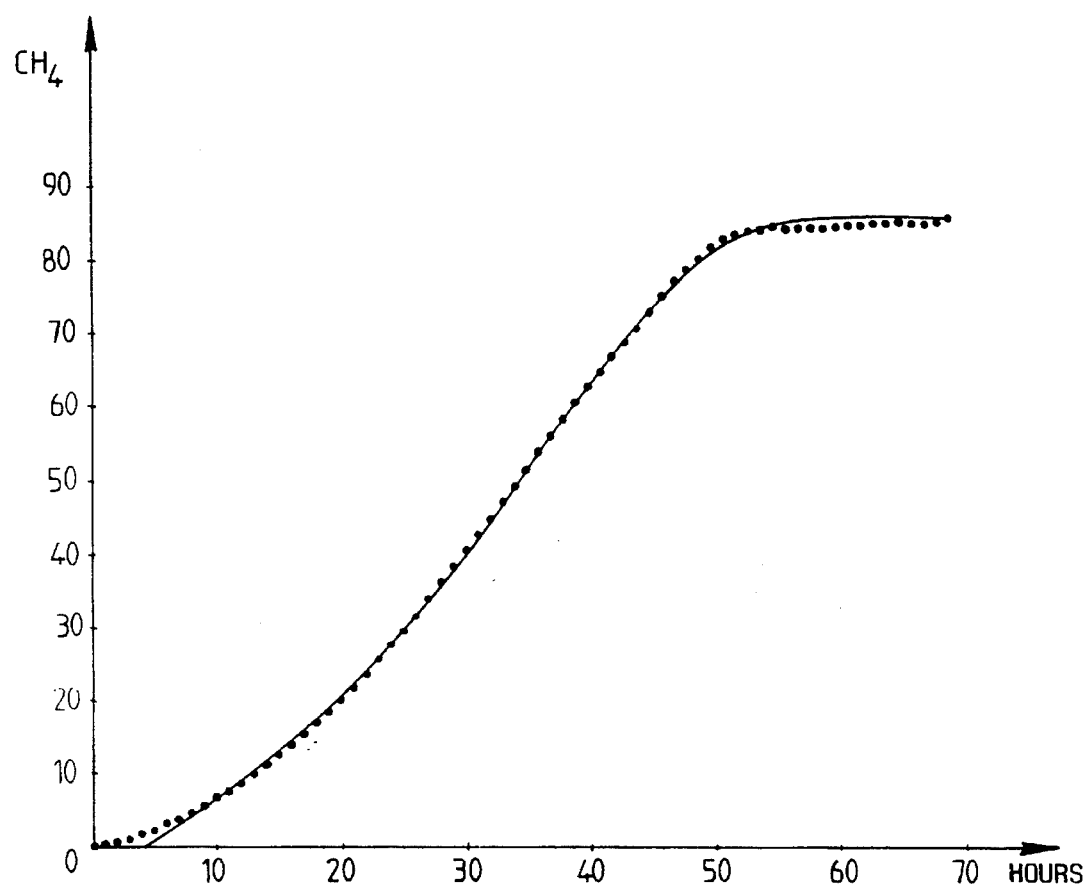

the pH and the acetate concentration;

FIG. 3 shows a curve representing the cumulated production of methane versus time.

DETAILED DESCRIPTION OF THE INVENTION

Figure 1:
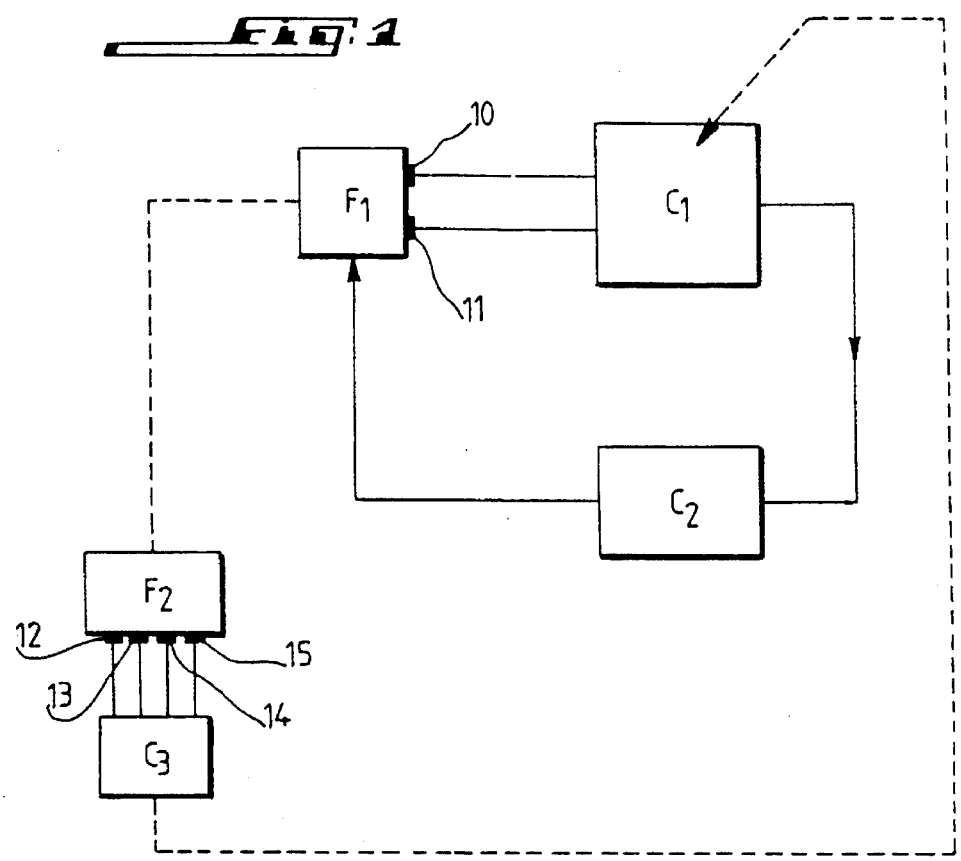
FIG. 1 is a block-diagram of an equipment according to the principles of the invention.

Referring to FIG. 1, there is seen an equipment for the control of the methanic fermentation of organic materials according to this invention, which essentially comprises a fermentor F1 with which are associated sensors 10, 11 to permit physical-chemical measurements to be made, namely in particular a measurement of the pH and a measurement of the content of volatile fatty acids.

The sensors 10, 11 are connected to a computer C1 processing these measurements with the assistance of a fermentation model.

The computer C1 which processes the aforesaid measurements and which provides a variable characterizing the biological state of the fermentor F1, is connected to another computer C2 which processes this variable to calculate a control mode to be applied to the fermentor F1.

At F2 is shown a small laboratory fermentor which may be filled with organic material from the fermentor F1 as physically shown by the dotted line between F1 and F2. With this fermentor F2 are associated sensors 12, 13, 14 and 15 themselves connected to one or several computers C3 processing the data from the sensors and providing the computer C1 with the adjusted values of the characteristic parameters of the fermentation model incorporated into the computer C1.

The F2-C3 assembly Forms an experimenting device on a reduced scale which as will be explained later in detail allows to automatically follow the evolution or development with time of the pH and of the volatile fatty acids concentration as well as the amounts of methane and of $CO_2$ produced.

The small fermentor F2 is fitted with means necessary for performing the aforesaid experimentation or testing on a reduced scale. These means (not shown) are in particular a means for introducing a direct substrate of the methanogenesis such as the acetic acid, conventional stirring, heating means, etc . . . .

The equipment which has just been described allows advantageously to follow the development of the methanic fermentation without the need of following the flow rate and the quality of the biogas produced by the fermentor F1 and this while performing on this fermentor measurements in a limited number only, namely essentially a measurement of the pH and a measurement of the content with volatile fatty acids. Moreover owing to the experimentation device F2-C3 it will be possible to easily adjust the parameters of the fermentation model to the local conditions (substrate, bacteria, operating conditions) governing the fermentation within the fermentor F1. It should also be pointed out that the data issued from the computer C1 are data which reflect the global state of the fermentation and which therefore allow via the computer C2 to achieve a control of the fermentation within the fermentor F1. This control could not be that effective or efficient if it were obtained directly from physical-chemical measurements issued from the sensors 10, 11.

Having described the equipment of FIG. 1, its operation will now be explained while recalling at first some principles of the methanic fermentation.

The methanic fermentation comprises four stages:

1. The hydrolysis of the substrate, the acidogenesis, the acetogenesis and the methanogenesis.

The hydrolysis step permits to convert if need be the complex molecules into simpler molecules.

The acidogenesis transforms these latter into fatty acids, alcohols, carbon dioxide and hydrogen.

The acetogenesis provides the conversion of the products of the acidogenesis into immediate precursors of methane such as the acetic acid.

The methanogenesis mainly provides the synthesis of methane from acetic acid according to the simplified formula:

$$CH_3COOH \rightarrow CH_4 + CH_2$$

According to the invention the fermentation model incorporated into the computer C1 and permitting to provide a characteristic variable of the biological state takes into account the coupling of the bacterial growth with the production of biogas, the inhibition of the growth of the methanogeneous bacteria by an excess of non-ionized acetic acid and acid-base equilibriums of the liquid and gaseous phases.

There exists a close relationship between the instantaneous methanogeneous activity $\mu$, the maximum methanogeneous activity $\mu_{max}$, the pH and the acetate concentration. This relationship is:

$$\mu = \mu_{max} \cdot \frac{[HS]}{K_S + [HS] + \frac{[HS]^2}{K_i}} \text{ with}$$

$$[H^+][S^-] - K_a \cdot [HS] = 0$$
$$[HS] + [S^-] - [S] = 0$$

where $\mu$ is the specific growth rate or factor of the methanogeneous bacteria consuming the acetic acid, $\mu_{max}$ is the maximum specific growth rate or factor of these same bacteria, $K_i$ is the inhibition constant, $K_s$ is the saturation constant,

[HS] is the concentration (g/l) of non-ionized acetic acid,

[S] is the concentration (g/l) of total acetic acid,

[H$^+$] is the pH value,

[S$^-$] is the concentration (g/l) of ionized acetic acid.

Therefore the above equations allow upon knowing the values measured in line or out of line of the pH and of the concentration of volatile fatty acids such as acetate to obtain the value of the methanogeneous activity.

Figure 2:
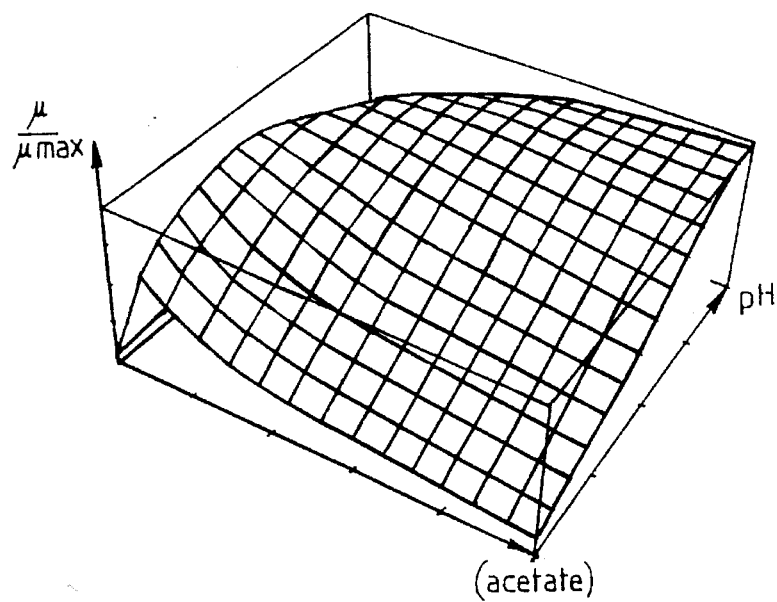
FIG. 2 shows a surface illustrating the relationship between the methanogeneous activity, $$\frac{\mu}{\mu_{max}},$$

Thus with given fermentation conditions, the fermentation model permits to calculate the value $$\frac{\mu}{\mu_{max}}$$

as a function of the pH and of the content with volatile fatty acids or acetate. FIG. 2 illustrates the relationship between these three parameters for a given substrate. Therefore when knowing the value or the pH and the content with volatile fatty acids by means of the sensors 10 and 11, the computer C1 determines the ratio.

$$\frac{\mu}{\mu_{max}}.$$

Then the information is conveyed to the computer C2 which contains mandatory instructions for the control of the fermentor F1, so that the computer C2 may act upon various members of the fermentor F1 such as a feed valve for instance.

When the adjustment of the fermentation model is necessary in view for instance of the change of the substrate, of the change of the operating conditions of the fermentor or also at the start of a new equipment, the device for experimentation on a reduced scale F2-C3 will be used according to the following procedure.

This procedure for the adjustment of the parameters of the model requires at most four tests by providing a range of acetic acid concentration and of pH ranging from little inhibiting conditions towards strongly inhibiting conditions of the methanogeneous bacteria.

By way of example these four tests are run by varying the initial value of the pH from 6.5 to 7 and the initial concentration of acetic acid for instance from 1 g/l to 15 g/l. The variations of the initial pH are obtained by adding hydrochloric acid at 10% into the fermentor whereas the variations of the initial concentration of acetate are obtained by adding a solution of acetic acid or of calcium acetate.

These additions are of course effected into the small fermentor F2 previously filled with material taken from the fermentor F1.

The table herebelow summarizes for instance the four tests carried out with a given substrate for the experimental enabling or validation of the model:

| initial pH | Acetic acid concentration (g/l) | State of the fermentation |
|---|---|---|
| 6.5 | 1 | not inhibited |
| 6.5 | 10 | inhibited |
| 7 | 10 | not inhibited |
| 7 | 15 | inhibited. |

For each one of these batch experiences, curves are then available, representing, versus time, the cumulated production of methane and of carbon dioxide within the small fermentor F2 as well as the variations in the pH and in the acetate content.

FIG. 3 shows by way of example one of the curves recorded during these experiments.

The dots represent the measured values. On the basis of the following equations describing the fermentation in the same experimental conditions, a method of adjustment is used, which permits to obtain the values of the characteristic parameters of this fermentation model while minimizing the deviation or difference between the measured values and the values calculated by the model. The solid line of FIG. 3 represents the simulated evolution or development for the experiment after this adjustment of the model.

$$[H^+] \cdot S^- - K_a \cdot HS = 0 \qquad (1)$$
$$HS + S^- S = 0 \qquad (2)$$
$$[H^+] \cdot B - K_a \cdot CO_{2d} = 0 \qquad (3)$$
$$B + CO_{2d} - IC - 0 \qquad (4)$$
$$B + S^- - Z = 0 \qquad (5)$$
$$\frac{dX}{dt} = \mu \cdot X \qquad (6)$$
$$\frac{dS}{dt} = -R_3 \cdot \frac{dX}{dt} \qquad (7)$$
$$\frac{dCH_{4cum}}{dt} = R_1 \cdot R_3 \cdot \mu \cdot X \qquad (8)$$
$$\frac{dICP}{dt} = R_2 \cdot R_3 \cdot \mu \cdot X \qquad (9)$$
$$\frac{dZ}{dt} = 0 \qquad (10)$$

With the following intermediate equations:

$$\mu = \mu_{max} \cdot \frac{HS}{V \cdot K_S + HS + \frac{HS^2}{K_i \cdot V}}$$

$$P_{CO2} = \frac{CO_{2d}}{V \cdot K_H}, \quad CO_{2cum} = CO_{2g} - CO_{2ini};$$

$$CO_{2g} = \frac{P_{CO_2}}{P_t - P_{CO_2}} (N_{2ini} + CH_4), \quad IC = ICP - CO_{2cum}$$

with

H$^+$: the concentration of ions H$^+$,

S: the amount of substrate (acetate),

HS: the amount of non-ionized acetate,

S$^-$: the amount of ionized acetate,

B: the amount of bicarbonates, $K_a$: the acidity constant of the acetic acid, $K_b$: the dissociation constant of the bicarbonates, $CO_{2d}$: the amount of dissolved carbon dioxide, IC: the amount of inorganic carbon, Z: the amount of cations, X: the amount of biomass, μ: the specific growth rate of the biomass, $R_3$: the output yield or efficiency expressed as the ratio substrate/biomass, $CH_{4cum}$: the amount of cumulated produced methane, $R_1$: the yield output or efficiency expressed as the ratio methane/biomass, ICP: the amount of inorganic carbon evolved, $R_2$: the yield output expressed as the ratio carbon dioxide/biomass, $P_{CP2}$: the partial pressure of carbon dioxide in the gaseous volume, $P_t$: the total pressure of the gaseous volume, $CO_{2cum}$: the amount of cumulated carbon dioxide, $\mu_m$: the maximum specific growth rate, $K_s$: the saturation constant, $K_i$: the inhibition constant, V: the volume of the fermentor of the experimental device, $K_H$: the Henry constant for the carbon dioxide, $CO_{2g}$: the amount of gaseous carbon dioxide, $CO_{2ini}$: the amount of initial carbon dioxide in the gaseous phase, $N_{2ini}$: the amount of initial nitrogen, IC: the amount of inorganic carbon.

The four first algebraic equations reflect the acid-base equilibriums of the two following pairs of respective equilibrium constants $K_a$ and $K_b$:

acetic acid/acetate;

produced dissolved carbon dioxide/bicarbonate.

The fifth algebraic equation represents the electroneutrality of the medium and introduces an additional variable Z which is the whole amount of the cations present in the fermentor.

The state variables of the model are the following: $H^+$, $HS^-$, $S^-$, B, $CO_{2d}$, X, S, $CH_{4cum}$, ICP and Z.

The value of the output yield or efficiency $R_2$ according to the ratio carbon dioxide/biomass is set to be equal to 1. The initial values of the pH, of the amounts of substrate S, methane and carbon dioxide, respectively, are measured.

A calculation from the algebraic equations then permits to obtain the initial values of the amounts of acetic acid HS, acetate $S^-$, bicarbonate B, dissolved carbon dioxide $CO_{2d}$, inorganic carbon IC, respectively, as well as the whole amount of the dissolved cations within the fermentor.

The acidity constants of the acetic acid $K_a$, of the dissolved $CO_2$ $K_b$ and of the Henry constant $K_H$ are adjusted from the experimental data.

In the example presented here, the values of these constants are the following:

$K_a = 1.7 \times 10^{-5} M$ $K_b = 1.7 \times 10^{-7} M$ $K_H = 0.065 M/atm$

The biological parameters of the model are the maximum growth rate $\mu_{max}$, the saturation constant $K_S$, the inhibition constant $K_i$, the output yield of methane with respect to the biomass $R_1$ and the output yield of substrate with respect to the biomass $R_3$. They are identified from the experimental data. The estimation of the parameters requires the integration of the model and the knowledge of the initial values of the state variables. The non-known and non measurable initial biomass is therefore considered as a parameter which is also identified and which is expressed as an arbitrary unit (UA).

Still in the example presented here with a given substrate and in relation to FIG. 2 are hereinafter given the values of the characteristic parameters of this fermentation model which have permitted to set up the surface of FIG. 2:

$\mu_{max} = 0.017$ 1/h $K_S = 2.18 \times 10^{-5} M$ $K_i = 8.22 \times 10^{-4} M$ $R_1 = 1 M/M$ $R_3 = 350$ mM/UA The invention is of course not at all limited to the embodiment described and illustrated which has been given by way of example only.

We claim:

1. Apparatus for controlling the methane fermentation of organic materials comprising a first fermentor in which the organic materials are situated, sensors coupled to said first fermentor for taking physical-chemical measurements of the material in said first fermentor, a first computer for processing these measurements and converting the measurements with the assistance of a fermentation model into a characteristic variable of the biological state of the organic materials in said first fermentor, said fermentation model constituting a function of the concentration of non-ionized acetic acid, the concentration of total acetic acid, the pH value and the concentration of ionized acetic acid in the organic materials, a second computer for controlling said first fermentor from said characteristic variable, and an experimentation device comprising a second fermentor containing a sample of material taken from said first fermentor, sensors coupled to said second fermentor for measuring data of the methane fermentation of said sample in said second fermentor and a third computer for processing the data from said sensors coupled to said second fermentor and for sending the data to said first computer, said fermentation model being adjusted in said first computer based on the methane fermentation data of said sample in said second fermentor.

2. The apparatus according to claim 5, wherein said first and second computers consist of a single computer.

3. The apparatus according to claim 1, wherein sensors coupled to said second fermentor continuously measure the pH, the amounts of $CH_4$ and of $CO_2$ produced and the concentration of volatile fatty acids within the second fermentor whereas the data provided by said third computer is:

the maximum specific methanogeneous growth rate ($\mu_{max}$), the inhibition constant of the methanogeneous bacteria ($K_i$), the saturation constant of the methanogeneous bacteria ($K_s$), and the output yields ($R_1$) expressed as the CH24/biomass ratio, ($R_2$) as the $CO_2$/biomass ratio and ($R_3$) as the substrate/biomass ratio, respectively.

4. The apparatus of claim 1, wherein said sensors coupled to said first fermentor measure the pH value and volatile fatty acids content of material therein.

5. The apparatus of claim 1, wherein said characteristic variable of the biological state of the organic materials in said first fermentor represents the methanogeneous biological activity of the biological state of said first fermentor.

6. The apparatus of claim 1, wherein said sensors coupled to said second fermentor measure the pH and concentration of volatile fatty acids of the material in the second fermentor and the amounts of $CH_4$ and $CO_2$ produced in the second fermentor.

7. The apparatus of claim 1, wherein said fermentation model is adjusted upon a change in the quantity of biomass present in said first fermentor and a change in the quantity of substrate being treated in said first fermentor.

* * * * *